United States Patent [19]

Scherberich

[11] 4,156,701
[45] May 29, 1979

[54] THIAZOLIDIN-4-CARBONITRILE

[75] Inventor: Paul Scherberich, Dietzenbach, Fed. Rep. of Germany

[73] Assignee: Deutsche Gold- und Silber-Scheideanstalt vormals Roessler, Frankfurt, Fed. Rep. of Germany

[21] Appl. No.: 840,713

[22] Filed: Oct. 11, 1977

[30] Foreign Application Priority Data

Oct. 9, 1976 [DE] Fed. Rep. of Germany ....... 2645692

[51] Int. Cl.² ........................................... C07D 277/04
[52] U.S. Cl. ............................................ 260/306.7 R
[58] Field of Search ................................. 260/306.7 R

[56] References Cited

U.S. PATENT DOCUMENTS

| 3,498,997 | 3/1970 | Laliberte | 260/306.7 R |
| 3,853,902 | 12/1974 | Raaslh | 260/306.7 R |

*Primary Examiner*—Nicholas S. Rizzo
*Attorney, Agent, or Firm*—Cushman, Darby & Cushman

[57] ABSTRACT

There are prepared thiazolidin-4-carbonitriles of the formula

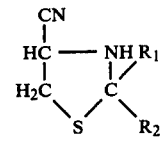

where $R_1$ and $R_2$ are alkyl, alkenyl, cycloalkyl, cycloalkenyl, aryl, aralkyl or aralkyl or one of $R_1$ and $R_2$ is hydrogen or $R_1$ and $R_2$ are joined together with the adjacent ring carbon atom to form a ring as well as salts thereof. The compounds can be hydrolyzed to form cysteine.

13 Claims, No Drawings

THIAZOLIDIN-4-CARBONITRILE

BACKGROUND OF THE INVENTION

The invention is directed to thiazolidin-4-carbonitriles substituted in the 2-position and salts of such compounds and a process for their production. The thiazolidin-4-carbonitriles of the invention are substituted once or twice.

The thiazolidin-4-carbonitriles of the invention are particularly those which have the formula

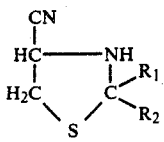

in which $R_1$ and $R_2$ are the same or different and individually are hydrogen or straight or branch chain alkyl or alkenyl groups with preferably up to 12 and particularly up to 4 carbon atoms, or are cycloalkyl or cycloalkenyl groups with preferably up to 6 carbon atoms or are aryl groups or aralkyl groups with up to 4, and especially up to 2 carbon atoms in each alkyl group with the proviso that not over one of $R_1$ and $R_2$ is hydrogen or $R_1$ and $R_2$ together with the adjacent ring carbon atoms form a ring, e.g., $R_1$ and $R_2$ together are an alkylene group of preferably 3 to 12 carbon atoms, and particularly 4 to 7 carbon atoms.

The alkyl groups include for example n-pentyl, n-hexyl, 2-ethylhexyl, n-octyl or n-dodecyl or especially methyl, ethyl, propyl, isopropyl, n-butyl, sec.butyl or tert.butyl; when $R_1$ and $R_2$ are joined together they form for example a trimethylene, tetramethylene, pentamethylene, hexamethylene or heptamethylene group; the alkenyl groups include for example hexen-(3)-yl-(1) or dodecen-(8)-yl-(1) or especially vinyl, allyl, methallyl or crotyl group; the cycloalkyl groups are for example cyclopropyl, cyclopentyl, cyclohexyl, cycloheptyl or cyclooctyl; the cycloalkenyl groups include for example cyclopropenyl, cyclopentenyl or cyclohexenyl; the aryl groups include for example phenyl or naphthyl; the aralkyl groups are for example phenylpropyl or especially benzyl or phenethyl; the alkaryl groups include for example 4-tert.-butylphenyl or especially p-tolyl, o-xylyl or 4-ethylphenyl.

Examples of the thiazolidin-4-carbonitriles within the invention include 2-methyl-thiazolidin-4-carbonitrile, 2,2-dimethyl-thiazolidin-4-carbonitrile, 2-ethyl-thiazolidin-4-carbonitrile, 2-methyl-2-ethyl-thiazolidin-4-carbonitrile, 2,2-diethyl-thiazolidin-4-carbonitrile, 2-methyl-2-n-propyl-thiazolidin-4-carbonitrile, 2-methyl-2-isopropyl-thiazolidin-4-carbonitrile, 2-phenyl-thiazolidin-4-carbonitrile, 2-o-xylyl-thiazolidin-4-carbonitrile, 2-cyclohexyl-thiazolidin-4-carbonitrile, 2,2-pentamethylene-thiazolidin-4-carbonitrile, 2-isopropyl-thiazolidin-4-carbonitrile, 2,2tetramethylene-thiazolidin-4-carbonitrile, 2,2-hexamethylene-thiazolidin-4-carbonitrile, 2,2-heptamethylene-thiazolidin-4-carbonitrile, 2,2-undecamethylene-thiazolidin-4-carbonitrile, 2,2-diphenyl-thiazolidin-4-carbonitrile, 2-methyl-2-phenyl-thiazolidin-4-carbonitrile, 2-p-tolyl-thiazolidin-4-carbonitrile, 2-o-ethylphenyl-thiazolidin-4-carbonitrile, 2-p-butylphenyl-thiazolidin-4-carbonitrile, 2-benzyl-thiazolidin-4-carbonitrile, 2,2-dibenzyl-thiazolidin-4-carbonitrile, 2-methyl-2-benzyl-thiazolidin-4-carbonitrile, 2-phenethyl-thiazolidin-4-carbonitrile, 2-naphthyl-(1)-thiazolidin-4-carbonitrile, 2-cyclopentyl-thiazolidin-4-carbonitrile, 2-methyl-2-cyclopropyl-thiazolidin-4-carbonitrile, 2-cyclohexenyl-thiazolidin-4-carbonitrile, 2-n-butyl-thiazolidin-4-carbonitrile, 2,2-di-n-butyl-thiazolidin-4-carbonitrile, 2-methyl-2-n-butyl-thiazolidin-4-carbonitrile, 2-methyl-2-sec.butyl-thiazolidin-4-carbonitrile, 2-dodecyl-thiazolidin-4-carbonitrile, 2-ethyl-2-dodecyl-thiazolidin-4-carbonitrile, 2-methyl-2-octyl-thiazolidin-4-carbonitrile, 2-vinyl-thiazolidin-4-carbonitrile, 2-methyl-2-vinyl-thiazolidin-4-carbonitrile, 2-allyl-thiazolidin-4-carbonitrile, 2-ethyl-2-allyl-thiazolidin-4-carbonitrile, 2-crotyl-thiazolidin-4-carbonitrile and 2-methyl-2-methallyl-thiazolidin-4-carbonitrile.

The salts of the invention of the thiazolidin-4-carbonitriles substituted in the 2-position are addition salts of the nitrile with organic and especially inorganic acids. The organic acids include aliphatic, alicyclic, aromatic or heterocyclic mono or polycarboxylic acids or sulfonic acids as for example formic acid, acetic acid, propionic acid, butyric acid, valeric acid, oxalic acid, malonic acid, succinic acid, glutaric acid, adipic acid, sebacic acid, glycolic acid, tartaric acid, malic acid, maleic acid, fumaric acid, citric acid, ascorbic acid, hydroxy maleic acid, pyruvic acid, phenyl acetic acid, benzoic acid, p-anthranilic acid, p-hydroxybenzoic acid, salicylic acid, p-aminosalicylic acid, methanesulfonic acid, ethanesulfonic acid, hydroxyethanesulfonic acid, halobenzenesulfonic acid, e.g., p-chlorobenzenesulfonic acid, toluenesulfonic acid, e.g., p-toluenesulfonic acid, or sulfanilic acid. The inorganic acids are especially mineral acids and chiefly strong mineral acids, as for example sulfuric acid, phosphoric acid and hydrohalic acids, e.g., hydrochloric acid and hydrobromic acid. Particularly well crystallizing salts are the hydrochlorides.

The thiazolidin-4-carbonitriles substituted in the 2-position according to the invention are produced from the corresponding thiazoline-(3) compounds of the formula

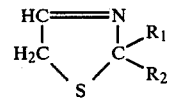

Suitable thiazolines for example are 2-methyl-thiazoline-(3)-, 2,2-dimethyl-thiazoline-(3), 2-ethyl-thiazoline-(3), 2-methyl-2-ethyl-thiazoline-(3), 2,2-dimethyl-thiazoline-(3), 2-methyl-2-n-propyl-thiazoline-(3), 2-methyl-2-isopropyl-thiazoline-(3), 2-phenyl-thiazoline-(3), 2,2-hexamethylene-thiazoline-(3), 2-cyclohexyl-thiazoline-(3), 2,2-pentamethylene-thiazoline-(3), 2-isopropyl-thiazoline-(3), 2,2-tetramethylene-thiazoline-(3), 2,2-heptamethylene-thiazoline-(3), 2,2-undecamethylene-thiazoline-(3), 2,2-diphenyl-thiazoline-(3), 2-methyl-2-phenyl-thiazoline-(3), 2-p-tolyl-thiazoline-(3), 2-o-ethylphenyl-thiazoline-(3), 2-p-butylphenyl-thiazoline-(3), 2-benzyl-thiazoline-(3), 2,2-dibenzyl-thiazoline-(3), 2-methyl-2-benzyl-thiazoline-(3), 2-phenethyl-thiazoline-(3), 2-naphthyl-thiazoline-(3), 2-cyclopentyl-thiazoline-(3), 2-methyl-2-cyclopropyl-thiazoline-(3), 2-cyclohexenyl-thiazoline-(3), 2-methyl-2-cyclohexenyl-thiazolidine-(3), 2-n-butyl-thiazoline-(3), 2,2-di-n-butyl-thiazoline-(3), 2-methyl-2-n-butyl-thiazoline-(3), 2-methyl-2-sec.butyl-thiazoline-(3), 2-dodecyl-thiazoline-(3), 2-ethyl-2-dodecyl-thiazoline-(3), 2-methyl-2-octylthiazoline-(3), o-xylyl-thiazoline-(3), 2-vinyl-thiazoline-(3), 2-methyl-2-vinyl-thiazoline-(3), 2-allyl-thiazoline-(3), 2-ethyl-2-allyl-thiazoline-(3), 2-crotyl-thiazoline-(3), 2-methyl-2-methallyl-thiazoline-(3).

These thiazolines can be prepared for example by reaction of mercaptoacetaldehyde with an oxo compound and ammonia (Asinger U.S. Pat. No. 2,879,273) or especially by reaction of (1) a halogenated acetaldehyde, e.g., chloroacetaldehyde with (2) an oxo compound, e.g., acetone, (3) a metal or ammonium hydrogen sulfide, e.g., sodium hydrogen sulfide and (4) ammonia (see Scherberich U.S. application Ser. No. 840,714 entitled "Process for the Production of Thiazoline-(3) Compounds" filed on even date and corresponding to German application No. P 26 45 731.8 filed Oct. 9, 1976). The entire disclosures of the Asinger patent and the Scherberich U.S. application are hereby incorporated by reference and are relied upon.

The thiazoline-(3) compound is reacted with hydrogen cyanide to form the thiazolidin-4-carbonitrile. The hydrogen cyanide is added as such in gaseous or liquid form or as a solution in water or an organic solvent or is produced directly from other compounds, for example by reacting an acid, e.g., hydrochloric acid or sulfuric acid with an alkali cyanide, e.g., sodium cyanide or potassium cyanide. There can be used substantially any proportions either stoichiometric or over or under stoichiometric amounts. Generally, it is suitable to employ at least 1 mole but not over about 10 moles of hydrogen cyanide per mole of thiazoline. Preferably there are used 1.1 to 1.5 moles of hydrogen cyanide per mole of thiazoline.

Although the reactants, i.e., the thiazoline-(3) and the hydrogen cyanide, can be used undiluted, it is advantageous to carry out the reaction in the presence of solvents such as water or inert organic liquids. As organic liquids there can be used for example alcohols, esters, ethers or aliphatic or aromatic hydrocarbons, or halogenated aliphatic or aromatic hydrocarbons. Examples of such inert organic liquids are methyl alcohol, ethyl alcohol, propyl alcohol, isopropyl alcohol, butyl alcohol, dimethyl ether, diethyl ether, dipropyl ether, dibutyl ether, methyl acetate, ethyl acetate, butyl acetate, methyl propionate, ethyl butyrate, hexane, octane, petroleum ether, benzene, toluene, xylene, chloroform, carbon tetrachloride, dichloroethylene, methylene chloride and chlorobenzene.

The reaction temperature in a given case is adjusted according to the reactants and the solvent. Generally, temperatures from about $-10°$ to $+250°$ C. are chosen. Preferred are temperatures between about 0° and 100° C., particularly from 10° to 50° C.

The thiazolidin-4-carbonitrile is separated from the reaction mixture for example by cooling the mixture or by driving off the solvent which in a given case may be present.

The salts of the thiazolidin-4-carbonitriles are produced by treating the thiazolidin-4-carbonitrile, in a given case directly in the reaction mixture resulting from the production of the thiazolidin-4-carbonitrile, with the acid in question. The acids can be used in widely varying amounts at random, both in stoichiometric as well as under and over stoichiometric amounts. Generally, it is suitable to use at least 1 mole but not more than 5 moles of acid per mole of thiazolidin-4-carbonitrile. Preferably there are used 1.1 to 1.5 moles of acid per mole of thiazolidin-4-carbonitrile. Conversely the salts of thiazolidin-4-carbonitrile can be converted by means of bases, e.g., sodium hydroxide or anion exchangers into the free thiazolidin-4-carbonitrile.

The thiazolidin-4-carbonitriles substituted in the 2-position and in a given case their salts serve particularly as starting materials for the production of D,L-cysteine to which they can be converted by treatment with mineral acids, e.g., hydrochloric acid, preferably at elevated temperature. The formation of D,L-cysteine from the thiazolidin-4-carbonitrile is disclosed in more detail and claimed in Offermanns and Scherberich application Ser. No. 840,715 entitled "Process for the Production of D,L-Cysteine" filed on even date and corresponding to German application No. P 26 45 748.7 filed Oct. 9, 1976. The entire disclosure of the Offermanns et al. application is hereby incorporated by reference and relied upon.

In this manner there is produced a D,L-cysteine of outstanding quality and purity which can be used for example directly for fodder purposes. It has excellent stability and surprisingly does not change even upon long storage while cysteine produced in the customary way readily converts to cystine.

Unless otherwise indicated all parts and percentages are by weight.

The process can comprise, consist essentially of or consist of the steps set forth with the stated materials.

DESCRIPTION OF THE PREFERRED EMBODIMENTS

Example 1

There were added dropwise 30 grams (1.1 moles) of liquid hydrogen cyanide to a solution of 115 grams (1.0 mole) of 2,2-dimethyl-thiazoline-(3) in 250 ml of diethyl ether. Meanwhile and for a further 60 minutes the temperature was held at 10° to 20° C. Then the diethyl ether was distilled off under reduced pressure. The yield of 2,2-dimethyl-thiazolidin-4-carbonitrile amounted to 138 grams, corresponding to 97% based on the 2,2-dimethyl-thiazoline-(3) added. The 2,2-dimethyl-thiazolidin-4-carbonitrile had a melting point of 49° to 51° C. It was ascertained to be homogeneous by thin layer chromatographic investigation. The elemental analysis was as follows (in weight percent):

|  | C | H | N | S |
|---|---|---|---|---|
| found | 50.90 | 7.10 | 19.82 | 22.17 |
| calculated as $C_6H_{10}N_2S$ | 50.66 | 7.08 | 19.69 | 22.54 |

Example 2

The procedure was the same as in Example 1 but there was led into the reaction mixture with cooling to 5° to 10° C. hydrogen chloride until the 2,2-dimethyl-thiazolidin-4-carbonitrile formed separated as the hydrochloride. This was a colorless, crystalline substance having a melting point of 125° to 128° C. The yield was 170 grams, corresponding to 95% based on the 2,2-dimethyl-thiazoline-(3) added. The 2,2-dimethyl-thiazolidin-4-carbonitrile hydrochloride proved to be homogeneous in thin layer chromatographic investigation. The elemental analysis was:

|  | C | H | N | S | Cl |
|---|---|---|---|---|---|
| found | 40.52 | 6.30 | 15.52 | 17.80 | 19.79 |

|                           | C     | H    | N     | S     | Cl    |
|---------------------------|-------|------|-------|-------|-------|
| calculated as C$_6$H$_{11}$N$_2$SCl | 40.33 | 6.20 | 15.67 | 17.94 | 19.84 |

Example 3

The 2,2-dimethyl-thiazolidin-4-carbonitrile was produced by the process of Example 1. 143 grams (1 mole) were dissolved in 500 ml of ethanol. This solution was treated with 118 grams (1.2 moles) of concentrated sulfuric acid with cooling. The sulfuric acid salt of 2,2-dimethyl-thiazolidin-4-carbonitrile separated out of the mixture as a colorless, crystalline substance. The yield was 220 grams, corresponding to 91% based on the 2,2-dimethyl-thiazolidin-4-carbonitrile added. The salt recovered sintered at about 140° C. and decomposed between 250° and 300° C. The elemental analysis was:

|                           | C     | H    | N     | S     | O     |
|---------------------------|-------|------|-------|-------|-------|
| found                     | 30.15 | 5.22 | 11.87 | 26.20 | 26.45 |
| calculated as C$_6$H$_{12}$N$_2$S$_2$O$_4$ | 29.98 | 5.03 | 11.65 | 26.68 | 26.63 |

Example 4

The 2,2-dimethyl-thiazolidin-4-carbonitrile was produced by the process of claim 1. 143 grams (1 mole) were dissolved in 600 ml of propanol-(2). This solution was treated under cooling with 175 grams (1.5 moles) of 85 percent ortho phosphoric acid. After the addition of diethyl ether the phosphoric acid salt of 2,2-dimethyl-thiazolidin-4-carbonitrile separated out as a colorless, crystalline substance. The yield was 210 grams, corresponding to 87% based on the 2,2-dimethyl-thiazolidin-4-carbonitrile added. The phosphoric acid salt had a melting point (decomposition point) of 110° to 115° C. The elemental analysis was:

|                           | C     | H    | N     | S     | P     |
|---------------------------|-------|------|-------|-------|-------|
| found                     | 30.56 | 5.52 | 11.90 | 12.98 | 12.39 |
| calculated as C$_6$H$_{13}$N$_2$SO$_4$P | 30.02 | 5.45 | 11.66 | 13.34 | 12.89 |

Example 5

The procedure was the same as in Example 1 except there were added 155 grams (1.0 mole) of 2,2-pentamethylene-thiazoline-(3) in 300 ml of methanol and 32 grams (1.2 moles) of liquid hydrogen cyanide. After distillation off of the methanol, wetting with diethyl ether and cooling to 0° C. the 2,2-pentamethylene-thiazolidin-4-carbonitrile crystallized out. The yield was 180 grams, corresponding to 99% based on the 2,2-pentamethylene-thiazoline-(3) added. The 2,2-pentamethylene-thiazolidin-4-carbonitrile had a melting point of 70° to 72° C. It was shown by thin layer chromatographic examination to be homogeneous. The elemental analysis was:

|                           | C     | H    | N     | S     |
|---------------------------|-------|------|-------|-------|
| found                     | 59.15 | 7.82 | 15.21 | 17.65 |
| calculated as C$_9$H$_{14}$N$_2$S | 59.30 | 7.74 | 15.36 | 17.58 |

Example 6

The 2,2-pentamethylene-thiazolidin-4-carbonitrile was produced by the process of Example 5. 183 grams (1 mole) of the nitrile were dissolved in 400 ml of ethanol. Hydrogen chloride gas was led into the solution with cooling. The 2,2-pentamethylene-thiazolidin-4-carbonitrile hydrochloride separated out as a crystalline substance. The yield was 210 grams, corresponding to 96% based on the 2,2-pentamethylene-thiazolidin-4-carbonitrile added. The hydrochloride recovered had a melting point (decomposition point) of 148° to 150° C. It was shown to be homogeneous in thin layer chromatographic examination. The elemental analysis was:

|                           | C     | H    | N     | S     | Cl    |
|---------------------------|-------|------|-------|-------|-------|
| found                     | 49.65 | 6.85 | 12.72 | 14.73 | 15.99 |
| calculated as C$_9$H$_{15}$N$_2$SCl | 49.41 | 6.91 | 12.80 | 14.65 | 16.20 |

Example 7

The procedure was the same as in Example 1 except there were added 129 grams (1.0 mole) of 2-methyl-2-ethyl-thiazoline-(3) in 300 ml of diethyl ether and 30 grams (1.1 moles) of hydrogen cyanide. After distillation off of the diethyl ether and cooling of the residue to 0° C. the 2-methyl-2-ethyl-thiazolidin-4-carbonitrile crystallized out. The yield was 153 grams, corresponding to 98% based on the 2-methyl-2-ethyl-thiazoline-(3) added. The 2-methyl-2-ethyl-thiazolidin-4-carbonitrile had a melting point of 45° to 47° C. The elemental analysis was:

|                           | C     | H    | N     | S     |
|---------------------------|-------|------|-------|-------|
| found                     | 54.02 | 7.54 | 17.60 | 20.76 |
| calculated as C$_7$H$_{12}$N$_2$S | 53.81 | 7.73 | 17.92 | 20.52 |

Example 8

In order to convert the 2-methyl-2-ethyl-thiazolidin-4-carbonitrile produced in Example 7 into the hydrochloride there was used the procedure of Example 6. The 2-methyl-2-ethyl-thiazolidin-4-carbonitrile hydrochloride recovered had a melting point of 115° to 118° C. The elemental analysis was:

|                           | C     | H    | N     | S     | Cl    |
|---------------------------|-------|------|-------|-------|-------|
| found                     | 43.81 | 6.70 | 14.25 | 16.50 | 18.57 |
| calculated as C$_7$H$_{13}$N$_2$SCl | 43.62 | 6.79 | 14.53 | 16.63 | 18.39 |

Example 9

The procedure was the same as in Example 1 except there were added 143 grams (1.0 mole) of 2,2-diethyl-thiazoline-(3) in 250 ml of diethyl ether and 32 grams (1.2 mole) of hydrogen cyanide. The yield of 2,2-diethyl-thiazolidin-4-carbonitrile was 140 grams, corresponding to 94% based on the 2,2-diethyl-thiazoline-(3) added. The 2,2-diethyl-thiazolidin-4-carbonitrile had a melting point of 38° to 40° C. The elemental analysis was:

|                           | C     | H    | N     | S     |
|---------------------------|-------|------|-------|-------|
| found                     | 56.68 | 8.01 | 16.70 | 18.52 |
| calculated as C$_8$H$_{14}$N$_2$S | 56.43 | 8.28 | 16.45 | 18.83 |

Example 10

The procedure of Example 6 was employed to convert the 2,2-diethyl-thiazolidin-4-carbonitrile produced in Example 9 to the hydrochloride. The 2,2-diethyl-thiazolidin-4-carbonitrile hydrochloride had a melting point of 115° to 116° C.

Example 11

The procedure was the same as in Example 1 except there were added 101 grams (1.0 mole) of 2-methyl-thiazoline-(3) in 250 ml of diethyl ether and 30 grams (1.1 moles) of hydrogen cyanide. The 2-methyl-thiazolidin-4-carbonitrile had a melting point of 32° C. The elemental analysis was:

|  | C | H | N | S |
|---|---|---|---|---|
| found | 46.62 | 6.30 | 21.07 | 25.87 |
| calculated as $C_5H_8N_2S$ | 46.84 | 6.28 | 21.85 | 25.01 |

Example 12

The procedure was the same as in Example 1 except that there were added 163 grams (1.0 mole) of 2-phenyl-thiazoline-(3) in 250 ml of diethyl ether and 30 grams (1.1 moles) of hydrogen cyanide. The yield of 2-phenyl-thiazolidin-4-carbonitrile was 175 grams, corresponding to 92% based on the 2-phenyl-thiazoline-(3) added. The 2-phenyl-thiazolidin-4-carbonitrile had a melting point of 88° to 90° C. The elemental analysis was:

|  | C | H | N | S |
|---|---|---|---|---|
| found | 63.24 | 5.38 | 14.56 | 16.79 |
| calculated as $C_{10}H_{10}N_2S$ | 63.12 | 5.29 | 14.72 | 16.85 |

What is claimed is:

1. A thiazolidin-4-carbonitrile compound of the formula

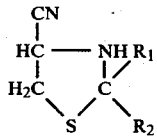

where $R_1$ and $R_2$ individually are hydrogen, alkyl of 1 to 12 carbon atoms, alkenyl of 2 to 12 carbon atoms, cycloalkyl of 3 to 6 carbon atoms, cycloalkenyl of 3 to 6 carbon atoms, phenyl, naphthyl, phenylalkyl with 1 to 4 carbon atoms in the alkyl group or alkylphenyl with 1 to 4 carbon atoms in the alkyl group or $R_1$ and $R_2$ together are an alkylene group of 3 to 12 carbon atoms or a salt thereof of an acid selected from the group consisting of monocarboxylic acids, polycarboxylic acids, sulfonic acids, sulfuric acid, phosphoric acid and hydrohalic acid.

2. A thiazolidin-4-carbonitrile compound of claim 1 in the form of the free base.

3. A thiazolidin-4-carbonitrile compound of claim 1 in the form of a salt.

4. A compound according to claim 1 wherein not over one of $R_1$ and $R_2$ is hydrogen.

5. A compound according to claim 4 wherein $R_1$ is hydrogen and $R_2$ is other than hydrogen.

6. A compound according to claim 4 wherein neither $R_1$ nor $R_2$ is hydrogen.

7. A compound according to claim 4 wherein $R_1$ and $R_2$ individually are hydrogen, alkyl of 1 to 4 carbon atoms, alkenyl of 2 to 4 carbon atoms, cyclohexyl, phenyl, naphthyl, alkyl phenyl having 1 to 2 carbon atoms in the alkyl or benzyl or $R_1$ and $R_2$ together are an alkylene group of 4 to 7 carbon atoms with the proviso that not over one of $R_1$ and $R_2$ is hydrogen.

8. A compound according to claim 1 wherein $R_1$ is hydrogen and $R_2$ is alkyl of 1 to 4 carbon atoms.

9. A compound according to claim 1 wherein $R_1$ and $R_2$ are both alkyl of 1 to 4 carbon atoms.

10. A compound according to claim 1 wherein $R_1$ is alkyl of 1 to 4 carbon atoms and $R_2$ is phenyl, tolyl, xylyl or ethyl phenyl.

11. A compound according to claim 1 wherein $R_1$ is hydrogen and $R_2$ is phenyl, tolyl, xylyl or ethyl phenyl.

12. A compound according to claim 1 wherein $R_1$ and $R_2$ are joined together and are pentamethylene.

13. A compound according to claim 7 wherein when the compound is in salt form the salt is of an acid selected from the group consisting of formic acid, acetic acid, propionic acid, butyric acid, valeric acid, oxalic acid, malonic acid, succinic acid, glutaric acid, adipic acid, sebacic acid, glycolic acid, tartaric acid, malic acid, fumaric acid, citric acid, ascorbic acid, hydroxy maleic acid, pyruvic acid, phenyl acetic acid, benzoic acid, p-anthranilic acid, p-hydroxybenzoic acid, salicylic acid, p-aminosalicylic acid, methanesulfonic acid, ethanesulfonic acid, hydroxyethane-sulfonic acid, p-chlorobenzenesulfonic acid, toluenesulfonic acid, sulfanilic acid, sulfuric acid, phosphoric acid, hydrochloric acid and hydrobromic acid.

* * * * *